US011357218B2

(12) United States Patent
Jansen et al.

(10) Patent No.: US 11,357,218 B2
(45) Date of Patent: Jun. 14, 2022

(54) BREEDING SYSTEM FOR CRAWLING INSECTS

(71) Applicant: Allmusca B.V., CL Bennebroek (NL)

(72) Inventors: Walter Lambert Jansen, Lisse (NL); Pieter Jacobus Alexander Faas, Lisse (NL)

(73) Assignee: ALLMUSCA B.V.

( * ) Notice: Subject to any disclaimer, the term of this patent is extended or adjusted under 35 U.S.C. 154(b) by 141 days.

(21) Appl. No.: 16/493,044

(22) PCT Filed: Mar. 15, 2018

(86) PCT No.: PCT/NL2018/050162
§ 371 (c)(1),
(2) Date: Sep. 11, 2019

(87) PCT Pub. No.: WO2018/169398
PCT Pub. Date: Sep. 20, 2018

(65) Prior Publication Data
US 2020/0008408 A1 Jan. 9, 2020

(30) Foreign Application Priority Data

Mar. 15, 2017 (NL) .................................... 2018526

(51) Int. Cl.
*A01K 67/033* (2006.01)
*A01K 1/00* (2006.01)
*F28F 27/00* (2006.01)

(52) U.S. Cl.
CPC .......... *A01K 67/033* (2013.01); *A01K 1/0082* (2013.01); *F28F 27/00* (2013.01)

(58) Field of Classification Search
CPC .............................. A01K 67/033; A01K 1/0082
(Continued)

(56) References Cited

U.S. PATENT DOCUMENTS

| 5,113,799 A | * | 5/1992 | Carr | ..................... | A01K 67/033 |
| | | | | | 119/6.5 |
| 8,091,510 B2 | * | 1/2012 | Hughes | ................ | A01K 63/003 |
| | | | | | 119/200 |

(Continued)

FOREIGN PATENT DOCUMENTS

| EP | 3 175 707 B1 | 11/2018 |
| WO | 2015/164240 A1 | 10/2015 |

(Continued)

OTHER PUBLICATIONS

Search Report for Netherlands Application No. NL 2018526, dated Sep. 14, 2017, pp. 1-8.

(Continued)

*Primary Examiner* — Monica L Barlow
*Assistant Examiner* — Aaron M Rodziwicz
(74) *Attorney, Agent, or Firm* — Thomas|Horstemeyer, LLP (57) ABSTRACT

The present invention relates to a breeding system for the breeding of crawling insects, comprising a drum, a shuffling device and a feeding device. The drum comprises at least one wall, defining a drum interior, to house the insects, and the shuffling device is arranged at least partially in the drum interior, to shuffle the insects. The feeding device id configured to feed nutrients into the drum interior. The system comprises a cooling device having a cooling fluid circuit that is, by means of a flow of coolant in the circuit, configured to withdraw heat from the drum interior. The invention further relates to a protein production system, for the on-site production of protein-rich insect larvae as animal feed, and to a method for the breeding of crawling insects, comprising the step of cooling the insects in the interior of the drum with a cooling device.

22 Claims, 4 Drawing Sheets

(58) Field of Classification Search
USPC .......................................................... 119/6.6
See application file for complete search history.

(56) References Cited

U.S. PATENT DOCUMENTS

| | | | |
|---|---|---|---|
| 9,642,344 B2* | 5/2017 | Unger | A01K 67/033 |
| 10,051,845 B1* | 8/2018 | Massaro | A01K 67/033 |
| 10,159,229 B2* | 12/2018 | Marchant | F21V 7/22 |
| 10,188,084 B2* | 1/2019 | Leo | A23K 20/174 |
| 10,912,288 B1* | 2/2021 | Hall | A01K 67/033 |
| 2011/0139075 A1 | 6/2011 | Shapiro et al. | |
| 2011/0174222 A1* | 7/2011 | Lee | A01K 67/033 |
| | | | 119/6.6 |
| 2014/0020630 A1* | 1/2014 | Courtright | A01K 67/033 |
| | | | 119/6.6 |
| 2014/0261188 A1* | 9/2014 | Chin | A01K 67/033 |
| | | | 119/6.6 |
| 2015/0122182 A1* | 5/2015 | Aldana | A01K 67/033 |
| | | | 119/6.6 |

FOREIGN PATENT DOCUMENTS

| | | | | |
|---|---|---|---|---|
| WO | WO-2015164240 A1 * | 10/2015 | ........... | A01K 67/033 |
| WO | 2016/015639 A1 | 2/2016 | | |
| WO | WO-2016015639 A1 * | 2/2016 | ........... | A01K 67/033 |

OTHER PUBLICATIONS

International Search Report & Written Opinion for PCT/NL2018/050162, dated Jul. 6, 2018, pp. 1-10.
International Preliminary Report on Patentability for PCT/NL2018/050162, dated Mar. 20, 2019, pp. 1-22.

* cited by examiner

BREEDING SYSTEM FOR CRAWLING INSECTS

CROSS-REFERENCE TO RELATED APPLICATIONS

This application is the National Stage of International Application No. PCT/NL2018/050162, filed Mar. 15, 2018, which claims the priority to NL 2018526, filed Mar. 15, 2017, which are entirely incorporated herein by reference.

The invention relates to a breeding system for crawling insects. These systems are adapted to facilitate the breeding and growth of insects. The insects may eventually be used as human food or animal feed, providing a nutrient that is rich in proteins. The growth cycle of the insect larvae results in various amounts of feed and water consumption over time and resulting heat production by the larvae.

Originally, these insects were bred on trays in a batch wise manner. However, the yield, and therefore the efficiency, of these systems was relatively low. In searching for alternatives, it has been found an alternative to breed insects in a drum-like breeding system. An example of such a system is known from prior art, for example from PCT-application WO2015/164240 A1.

This publication discloses a system for breeding insects, in particular for breeding black soldier flies, comprising a cylindrical barrel and a migration path therein. Eggs of the insects are brought in the barrel, after which larvae hatch from the eggs. These larvae are fed by the system, allowing them to grow up to a certain size. When they have reached this predefined size, they tend to migrate through an opening that is provided in a barrel wall, after which they are further processed, for example to be consumed by animals.

It has however been found that the yield of insects in this drum-like breeding unit is limited by excessive heat generation caused by the larvae in the drum. The known breeding units of WO2015/164240 A1 use air to cool the growing insect larvae by means of natural convection. Air is, however, able to cool only a limited mass of insect larvae; approximately up to a height of the mass of 15 centimetres.

It is therefore an object of the invention to provide a breeding system that lacks the above-mentioned disadvantage or at least to provide an alternative, preferably an alternative with an improved insect yield.

The invention provides a breeding system for the breeding of crawling insects, comprising:
a drum, comprising at least one wall, defining a drum interior, to house the insects,
a shuffling device, arranged at least partially in the drum interior, to shuffle insects in the drum interior,
a feeding device, to feed nutrients into the drum interior, characterized in that the system comprises a cooling device having a cooling fluid circuit that is, by means of a flow of coolant in the circuit, configured to withdraw heat from the drum interior.

With the system according to the invention, at least part of the heat that is generated by the insects is actively withdrawn from the drum interior. By doing so, the temperature of the insects in the drum can be kept lower and controlled better due to the improved heat dissipation, giving rise to better breeding conditions for the insects. As a result of the active cooling by the cooling device, a larger amount of insects can be bred in a breeding system according to the invention with similar dimensions as previously-known systems that lacked the cooling device.

The system according to the present invention may be able to effectively cool an insect mass with a height of up to 50 centimetres, preferably 100 centimetres and most preferable up to 200 centimetres. As such, the yield of the breeding systems according to the invention may be increased.

The breeding system according to the present invention is adapted to breed insects in a batch-wise manner. This means that, at a certain moment, a single batch of insect eggs or young insect larvae is brought in the drum, instead of the continuous feed in the prior art breeding system. Throughout the batch, the eggs or larvae all have a substantially the same age. In the drum, the insects will grow and will, due to their age being substantially the same, all go simultaneously through the same phases of growth.

During growth of the insects, in particular during the batch-wise growth in the enclosed breeding system, their behaviour under controlled conditions is predictable to a large extent. This means that, over time, the growth of the insects is substantially the same for each subsequent batch of insects that is bred.

Accordingly, the requirements for the insects are highly predictable for each batch under controlled conditions as well. The insects thus provide that, during their growth cycle, the required of feed, water and cooling is predictable and that the breeding system may be configured to control these parameters on a feedforward basis, without the constant need of measuring the actual condition of the insects.

The drum of the system may be a cylindrical drum, preferably a drum that is fixed to a frame of the system and being adapted to remain stationary with respect to its surroundings. In an embodiment however, the drum may have a rectangular-shaped upper portion, comprising four walls, and a semi cylindrical lower portion, which are connected to each other. This shape of drum provides the advantage that fewer edges will be present in the lower portion of the drum, so less dirt or contamination may remain in the drum after use and a less excessive cleaning would be sufficient. Furthermore, this shape of drum provides for easier shuffling of the insects, in particular when a radius of the shuffling device substantially corresponds to a radius of the cylindrical portion of the drum.

In an alternative embodiment, the drum may be a substantially cylindrical drum that is suspended in a frame, wherein the drum is rotatable around a central axis.

The shuffling device may be a screw, auger, ribbon mixer or paddle blender which is arranged in the interior of the drum. A thread along an outer contour of the screw, auger or ribbon mixer may have a spiral shape, such that, upon rotation of it around a central axis, the thread is configured to displace objects between the threads in a direction parallel to the central axis.

The screw, auger or ribbon mixer are, with their threaded portions, brought between the insects in the drum interior, such that these insects are moved, upon rotation of the shuffling device. A motor, such as an electric or hydraulic motor may be connected to the shuffling device to induce this rotation. The motor is preferably arranged outside the drum interior, for example to allow for easy access in case of malfunction, but may be arranged in the drum interior as well.

The paddle blender comprises paddles, which are, set at a distance, connected to a central rotational axle. The paddles are, upon rotation of the central axle, configured to shuffle the insects.

By shuffling the insects with the shuffling device, the insects in the drum interior are displaced and homogenized. The shuffling will provide a more evenly spread moisture and feed level in the drum interior, to thereby homogenize the breeding conditions of the insects and to allow for a constant, high-quality insect yield.

Furthermore, the shuffling will provide for a more evenly-spread temperature across the drum. It may be apparent that the temperature of the insects in the drum will be lower at free surfaces of the heap of insects, where heat can be dissipated to the ambient air, compared to an interior of the heap. By shuffling the insects, the heat is spread and it is continuously changed which insects are at the free surfaces of the heap.

Accordingly, the shuffling device provides, as a result of the improved cooling performance of the device, the advantage that a larger amount of insect larvae may be bred in each batch. The shuffling device may further provide the possibility to provide exact cooling on the basis of the predicted heat production by the insect larvae during their growth.

The shuffling device according to the present invention provides a further advantage over the breeding drum from the mentioned prior art document WO2015/164240 A1. Hence, the shuffling device according to the present invention is preferably adapted to mix the insects and distribute heat, moisture and food evenly over the entire mass. In the rotating breeding drum from WO2015/164240 A1, however, the mixing is based on the constant tumbling of the insects in the drum. In case insects stick together, they will not be mixed, but will remain attached to each other and will continue to rotate along with the drum.

The shuffling device may provide an oscillating movement to locate the insect larvae on one side of the drum when the larvae are small and to spread the larvae across the surface of the drum when they have grown and when their volume has been increased.

It is remarked that any suitable type of shuffling device may be used to shuffle the insects, whereby it is preferably avoided that the insects will be harmed and/or damaged during shuffling. Furthermore, a shuffling speed (e.g. rotational velocity of the device) must be kept relatively low to prevent the insects from being harmed.

In an embodiment, the shuffling device comprises multiple, preferably two, screws or augers, which are both arranged in the drum interior at least partially. The multiple screws or augers may be driven by a single motor, but preferably each of them is driven by a separate motor, allowing the different screws or augers to be driven independent of each other.

Preferably, both screws are configured to rotate in opposite directions during shuffling, such that insects are moved in a first direction with a first one of the screws, and moved in an opposite second direction with a second one of the screws. As such, the insects will be moved back and forth through the drum interior by the screws.

By arranging a shuffling device in the drum interior, it is no longer required to provide a rotatable drum with a spiral extending along its wall for mixing the insects, as was the case in WO2015/164240 A1. A more simple, and therefore less expensive, breeding system will thus be provided.

In a preferred embodiment, the drum is fixed with respect to its surroundings, as opposed to the rotatable drum of the prior art breeding system of WO2015/164240 A1. The shuffling device is thereby movable with respect to the drum in order to achieve the shuffling of the insects through the drum interior, without having to move, in particular without having to rotate, the entire drum.

With the feeding device, possibly in combination with the shuffling device, nutrients may be fed into the drum interior. To do so, the feeding device may comprise a conveyor to provide solid feed and/or a closable supply channel for feeding liquid nutrients to the insects.

In order to optimize feeding conditions for the insects, the feeding device may be configured to selectively feed nutrients in a continuous manner or a batch-wise manner, or a combination thereof, based on the needs of the insects.

Due to the predictable growth of the insects, in particular in a batch wise process, the feed requirements of the insects are predictable as well. The feeding device may thus be configured to determine the feeding requirements on a feedforward basis and to feed the insects on the basis of the predicted feeding requirements.

The cooling device comprises a cooling circuit having a cooling fluid circuit. In the cooling circuit, a coolant flows at a certain rate, wherein the rate may depend on the amount of cooling that is required. This cooling circuit may, for example, be a spirally-shaped channel which is arranged in the drum interior. As such, an outer wall of the cooling circuit is in contact with the insects in the drum interior, and heat can be exchanged through the outer wall of the circuit.

The cooling device is configured to control the temperature and/or the flow rate of the coolant that enters the cooling circuit. The coolant entering the cooling circuit may have a temperature that is lower than the temperature of the insects in the drum interior. Due to this temperature difference between the coolant and the insects, a heat flow may be induced from the insects towards the coolant.

When passing through the cooling circuit that is in contact with the drum interior, the temperature of the coolant is increased, while the temperature of the insects is thereby lowered. At some point in the circuit, the temperature of the coolant will approach that of the insects, thereby gradually reducing the heat flow.

By altering the flow rate of the coolant through the cooling circuit and/or by changing the entry temperature of the coolant entering the cooling circuit, the amount of heat that is withdrawn from the insects per unit time may be altered. As such, the heat flow from the insect to the coolant is adaptable to optimally suit a certain state and/or requirement of the insects.

In an embodiment, the system comprises a control unit that is adapted to control the cooling device and the feeding device on the basis of a phase of growth of the insects, in order to control the temperature in the drum interior. This control unit may thereby act as a feedforward controller that is configured to control the cooling and the feeding of the insects on the basis of a predicted setting.

The insects in the drum of the system are, during growth in batches, substantially in the same phase of growth and may have a substantially the same size. The needs or requirements of the insects, in particular the required amount of feed, water and/or cooling, are therefore substantially the same as well for every insect in a respective batch. The requirements for the insects vary over time, depending on the phase of growth, but these variations are predictable for respective breeds of insects.

The control unit is adapted to control the cooling device and the feeding device in a feedforward manner, on the basis of the predicted requirements for the insects. This feedforward control provides for optimal conditions for the insects and does not require the measurement of the actual temperature in the drum interior.

The control unit furthermore provides the advantage that the production conditions can be kept constant for each subsequent batch of insects. The insects that are formed at the end of the growth process are discharged from the system may thus be constant in quality and size.

With the control unit, the amount of insects in the batch may be determined as well. This may be done on the basis of a response, for example in temperature level, of the insects to the feeding of a certain amount of feed and/or water. The insects produce a certain amount of heat per unit of weight. In particular young insects, e.g. insects that have just been hatched from their eggs, produce a known amount of heat.

By determining the total amount of heat that is produced by all insects together, the amount of insects, e.g. in terms of mass and/or quantity, in the drum interior may be derived.

Finally, the growth rate, and thus the heat production, of the insects is related to the amount of feed that is fed into the drum interior. The temperature in the drum interior, being influenced by the heat production of the insects, can thus be controlled by controlling of the feeding with the feeding device. Hence, when a low amount of feed were to be fed to the insects, their growth rate and heat production would be low as well. In case a high amount of feed were to be fed to the insects, their growth rate and heat production would be larger.

In addition or as an alternative, the system comprises at least one temperature sensor. This sensor is configured to measure a temperature in the drum interior and to transmit a signal based on this temperature. The system further comprises a control unit, which is configured to control the temperature in the drum interior.

The control unit may, based on a measured temperature of the at least one temperature sensor, determine whether, and to what extent, the cooling device needs to cool the drum interior. By controlling the cooling device, the control unit determines whether, and to what extent, heat is to be withdrawn from the drum interior by the cooling device.

For example, in case the temperature in the interior of the drum is too high, the cooling device may be controlled to increase the cooling rate, which is the amount of withdrawn heat per unit of time. However, when the temperature becomes lower, approaching a desired temperature level, or when the temperature reaches the desired temperature level, the cooling device may be controlled to reduce the cooling rate. In case the temperature in the interior of the drum is below the desired temperature level, the cooling device may be controlled to reduce the cooling rate or even suspend the cooling, allowing the temperature to increase.

The control unit may thereby measure the temperature in the drum interior, such that the cooling device is controllable with a feedback-type control loop. A desired temperature, or temperature trajectory over time, may be programmed in the control unit. The control unit may then control the cooling to follow this predefined temperature or temperature trajectory.

In an embodiment, the cooling fluid circuit is arranged at least partially in the at least one wall of the drum. Thereto, the at least one wall of the drum may have a double wall, in between which the coolant may flow.

As a result, heat is withdrawn from the insects through the wall of the drum. By doing so, the entire wall surface of the drum will be an interface for heat-exchange and a large interfacial area is provided through which the heat may be withdrawn from the insects.

Having this large interfacial area is beneficial for removing large amounts of heat from the insects. In particular when a large flow of coolant through the cooling circuit is used, with a relatively low entry temperature, the heat flow may be large. Accordingly, a relatively large amount of insects, giving rise to a high amount of produced heat, may be bred in the breeding device.

In an embodiment, the shuffling device is configured to shuffle insects in the drum interior to homogenize the withdrawal of heat from the drum interior. The shuffling device is thereby configured to induce a circulating flow of insects. For example, a flow of insects along the inner wall will be in one direction, whereas a flow through a middle portion of the drum interior will be in the opposite direction.

The internal heat transport through the insects themselves is relatively low, compared to the heat transport from the insects through the wall. When the insects were not to be shuffled, only heat would be withdrawn from the insects that are in the vicinity of the wall and a boundary layer of insects with a lower temperature than those in the bulk of the heap would be created.

By shuffling the insects along the walls, it is changed which insects are in the boundary layer. As such, the internal heat transport through the insects is improved and the temperature of the insects is homogenized.

In an embodiment, the breeding system comprises a humidity sensor to measure the humidity in the drum interior. Based on the measured humidity, the control unit may change the cooling rate of the cooling device, and/or it may change a feed rate of the feeding device in order to adapt the conditions in the drum interior.

In an embodiment, the system comprises a moisture sensor to measure the moisture level in the drum interior. The moisture level differs from the humidity in that the humidity is a measure for the amount of water (vapour) in the air in the drum interior, while the moisture level is a measure for the amount of water that is present between the insects in the drum interior.

The control unit is adapted to change a feed rate of nutrients, in particular the rate at which water is added into the drum, based on a measured signal of the moisture level. As such, the control unit controls the moisture level between the insects in the drum interior.

Preferably, however, the control unit is configured to control the moisture level in between the insects in a feedforward manner, which means that the water supply to the insects in the drum interior is determined up front, on the basis of predicted requirements for the insects.

In an embodiment, the control unit is in contact with a central computer, which may not necessarily form part of the breeding system. For example, this computer may be arranged at a central location and may be remotely in contact with a plurality of breeding systems.

The central computer may receive sensor data from the control unit of each of the plurality of breeding systems and may receive information on parameters and insect yield of each of the breeding systems. As such, the central computer may self-learn which temperature, humidity, moisture level and/or feed rate are optimal in breeding as much insects as possible. Accordingly, the computer may share these optimal conditions with all breeding units, to program them for achieving the highest possible yield of insects.

Preferably, the central computer is configured to determine the required feeding and cooling profile during the growth cycle of the insects, on the basis of the collected data from multiple growth cycles of one or more breeding systems. Accordingly, the central computer may return these optimal feeding and cooling profiles towards the individual breeding systems in order to increase the yield of these systems.

In an embodiment, the control unit is configured to control the temperature in the drum interior such that the breeding system thereby becomes suitable to breed various species of crawling insects, in particular crawling larvae of flying insects, since the parameters of the climate in the drum interior may be adapted. In a preferred embodiment, the breeding system is at least suitable to breed housefly larvae therein, but it may be suitable as well to breed black soldier fly larvae or larvae of any other type of crawling insects.

In an embodiment, the drum comprises a discharge opening in the at least one wall. The shuffling device may be configured to discharge insects from the drum interior through the discharge opening, in order to empty the drum interior after the insects have grown to a certain predefined size.

The discharge opening is preferably arranged in the lower portion of the drum, in order to allow all insects to be discharged easily. For emptying the drum interior, the shuffling device may be configured to move different from how it moved during shuffling of the insects. For example, when the shuffling device comprises two screws, both screws may rotate in the same direction during emptying of the drum, instead of in opposite directions during shuffling of the insects.

In an embodiment, the shuffling device is a ribbon mixer, which comprises a first set of rigid ribbons, comprising an outer ribbon and an inner ribbon. The outer and inner ribbons are shaped as a strip, which spirally extends through the interior of the drum. The inner ribbon is thereby set radially inward in the drum interior, seen from the outer wall of the drum.

The outer ribbon may be configured to move the insects in the drum interior in a first direction, for example towards the discharge opening, and the inner ribbon may be configured to move the insects in a second direction, opposite to the first direction.

Preferably, the outer ribbon is configured to scrape sticking insects from the drum walls. This contributes to the homogenization of the insects and provides that all insects in the drum interior are shuffled.

In another embodiment, the shuffling device is a different ribbon mixer, which comprises a second set of rigid ribbons. The second set of ribbons comprises, just as the first set of ribbons, two rigid ribbons which spirally extend through the interior of the drum. The ribbons of the second set may be set at an angle, around the central axis, with respect to the first set. For example, this angle is 90°.

The shuffling device may be configured to discharge substantially all insects from the drum interior in a batch wise manner. Bo doing so, all insects are removed from the drum interior at the same time, when they have grown up to a certain size and when they are ready to be processed further.

In an embodiment, the breeding system comprises a fly cage and an egg-laying device. The fly cage and the egg-laying device may both be arranged on top of the drum and flies from the fly cage are promoted to lay eggs in the egg-laying device.

The flies are thereby housed in a different compartment than that in which the crawling insects are. The fly cage, furthermore, is a substantially closed-off compartment, only comprising a passage towards the egg-laying device, in order to prevent the flies from escaping.

The climate in the egg-laying device is chosen such, that it is optimal to promote the flies to lay eggs. The eggs of the insects are thereby accumulated in the egg-laying device and the egg-laying device may be configured to deposit eggs into the empty drum interior of the breeding system when a previous batch of fully-grown insects has been discharged from the drum interior. By doing so, the insects in the drum interior are grown in a batch wise manner, since the eggs are deposited in the drum at substantially the same time and are discharged at substantially the same time as well. Additionally, the eggs may first hatch in the egg-laying device, after which the just-hatched insects are discharged into the drum interior. With just-hatched insects, insects may be meant that have been hatched from their eggs, less than 24 hours ago.

In an embodiment, the control unit is configured to control the feeding device in order to feed a desired mass of nutrients to the insects in the interior of the drum, on the basis of the amount of the insects in the interior of the drum. The amount of nutrient is thereby optimally adapted to the growth of the insects, in order to provide the right amount of nutrients to the insects.

The invention further relates to a protein production system, for the on-site production of protein-rich live insect larvae that can for example be used as animal feed. With on-site, it is meant that the protein production system is intended to be placed at, or at least near the location at which the produced larvae are intended to be used, for example to be fed to the animals. This on site production provides that no, or at most little transportation of the live insects is required after they have been discharged from the breeding system.

The protein production system comprises two or more breeding systems as described above, which are arranged in a predefined space. The combined breeding systems are together configured to discharge living larvae in order to feed animals.

The location may be a chicken farm, wherein the larvae are fed to the chicken, in addition to conventional chicken feed. Alternatively, the larvae may be produced at a fish farm, to be fed to the fish.

In an embodiment, the protein production system comprises three or more breeding systems in the predefined space. This predefined space may have the dimensions of a standard-sized forty-feet shipping container, allowing for easy handling. By arranging the breeding system in the predefined space, the complete protein production system can be swiftly placed at the desired location, reducing, or even taking away, the need for on-site assembly.

In a preferred embodiment, the predefined space is a standard-sized forty-feet shipping container. Such containers do provide a rigid casing for the breeding units and can be handled easily due to corner castings at their corners, in which a twistlock-connector may be inserted and locked.

The invention further relates to a method for the breeding of crawling insects, comprising the steps of:
arranging insect eggs and/or insects that have been hatched from the eggs in an interior of a drum,
shuffling insects that were hatched from the eggs to homogenise a temperature of the insects, and
feeding the insects,
characterized in that, the method comprises the step of cooling the insects in the interior of the drum with a flow of coolant in a cooling circuit of a cooling device.

With the method according to the invention, a relatively large amount of insects can be bred in a relatively small breeding system. The insects can thus be bred more efficient and a higher insect yield may be achieved, compared to previous breeding methods.

With the step of cooling the insects in the interior of the drum, the heat that is produced by the insects is actively transported away from the insects with a flow of coolant in a cooling fluid circuit. The active cooling provides that more heat can be removed, compared to previous breeding methods, which relied on natural convection for the removal of heat.

In an embodiment, the method comprises the step of controlling the cooling device and the feeding device on the basis of a predicted growth profile of the insects, thereby controlling the temperature in the drum interior. In a respective batch, the growth profile is substantially the same for all insects, which provides that the requirements for all insects, in particular the required amount of feed, water and/or temperature, are substantially constant as well and may be known and predictable for respective breeds of insects.

The controlling is done in a feedforward manner, on the basis of the predicted requirements for the insects. The controlling thereby provides for optimal conditions for the insects in the drum interior. A further advantage lies in the fact that the step of measuring the actual temperature in the drum interior, and controlling on the basis of real-time sensor signals, is not required.

The feedforward controlling furthermore provides the advantage that the production conditions can be kept constant for each subsequent batch of insects. The insects that are subsequently bred according to the method may thus be constant in quality and size.

With the method, the amount of insects in the batch may be determined by measuring the amount of heat that is produced by the insects. A response in temperature level of the insects is then measured, which response is then compared to known temperature responses for various reference amounts of insects. From the comparison, an estimation follows on how many insects are present in the drum interior.

This estimation of the amount of insects in the drum interior can be used to select or determine the feedforward parameters used to control this specific batch. If, for example, a large amount of insects is present in the drum, for example the required amount of nutrients and water is larger, compared to when a small amount of insects were to be present.

Finally, the growth rate, and thus the heat production, of the insects is related to the amount of feed that is fed into the drum interior. The temperature in the drum interior, being influenced by the heat production of the insects, can thus be controlled by controlling of the feeding of the insects.

In an embodiment, the method comprises the step of loading the eggs in the interior of the drum out of an egg-laying device. The eggs are laid in the egg-laying device by flying insects, such as flies. In the egg-laying device, eggs are accumulated and stored until they can be received in the drum.

By opening the egg laying device for a restricted time, it is achieved that all eggs hatch at substantially the same time in the drum interior. The growing and breeding of the insects thereby becomes easier, as all insects in the drum interior do have an age that is substantially the same.

In an alternative embodiment, the egg-laying device is configured to promote substantially simultaneous hatching of the eggs therein. The just-hatched insects may then be kept in the egg-laying device, after which they may be discharged into the drum interior.

In an embodiment, the method comprises the step of discharging the insects from the interior of the drum when the insects have grown up to the predetermined size. All insects in a respective batch are thereby discharged from the drum interior at substantially the same time, which provides, in particular when their eggs have been hatched at the same time as well, that the discharged insects do have an age that is substantially the same. Accordingly, it may be assumed that the quality of the insects, in terms of size, protein content etc., is substantially constant as well.

In an embodiment, the method comprises the step of measuring temperature, humidity and/or moisture level in the interior of the drum. By doing so, the conditions of the insects and the environment in which they are bred may be monitored more accurately.

In a further embodiment, the method comprises the step of controlling the amount of cooling of the interior of the drum and of controlling the amount of feeding to the insects, based on the measured temperature, humidity and/or moisture level.

In a further embodiment, the method comprises the step of measuring the temperature of the insects and of controlling the amount of cooling with the cooling device, based on the measured temperature.

By controlling the amount of cooling, and measuring the temperature after each controlling step, a feedback-type of controller is obtained. This feedback controller may act on a change in temperature of the insects. Furthermore, the feedback controller is configured to follow a predefined temperature trajectory that is programmed in the system. By comparing the actual temperature of the insects and a desired temperature at that moment, the control unit may decide whether additional cooling by the cooling device is needed or not.

By controlling all these parameters, the condition of the insects in the drum interior can be controlled more accurately, as compared to when only the temperature were to be a measured parameter or when no controlling were to be present at all. In the end, a higher and more constant yield of insects may be achieved, wherein the insects may have a substantially higher quality as well.

Further characteristics of the breeding system according to the invention will be explained below, with reference to embodiments thereof, which are displayed in the appended drawings, in which.

Throughout the figures, the same reference numerals are used to refer to corresponding components or to components, which have a corresponding function.

Figure 1:
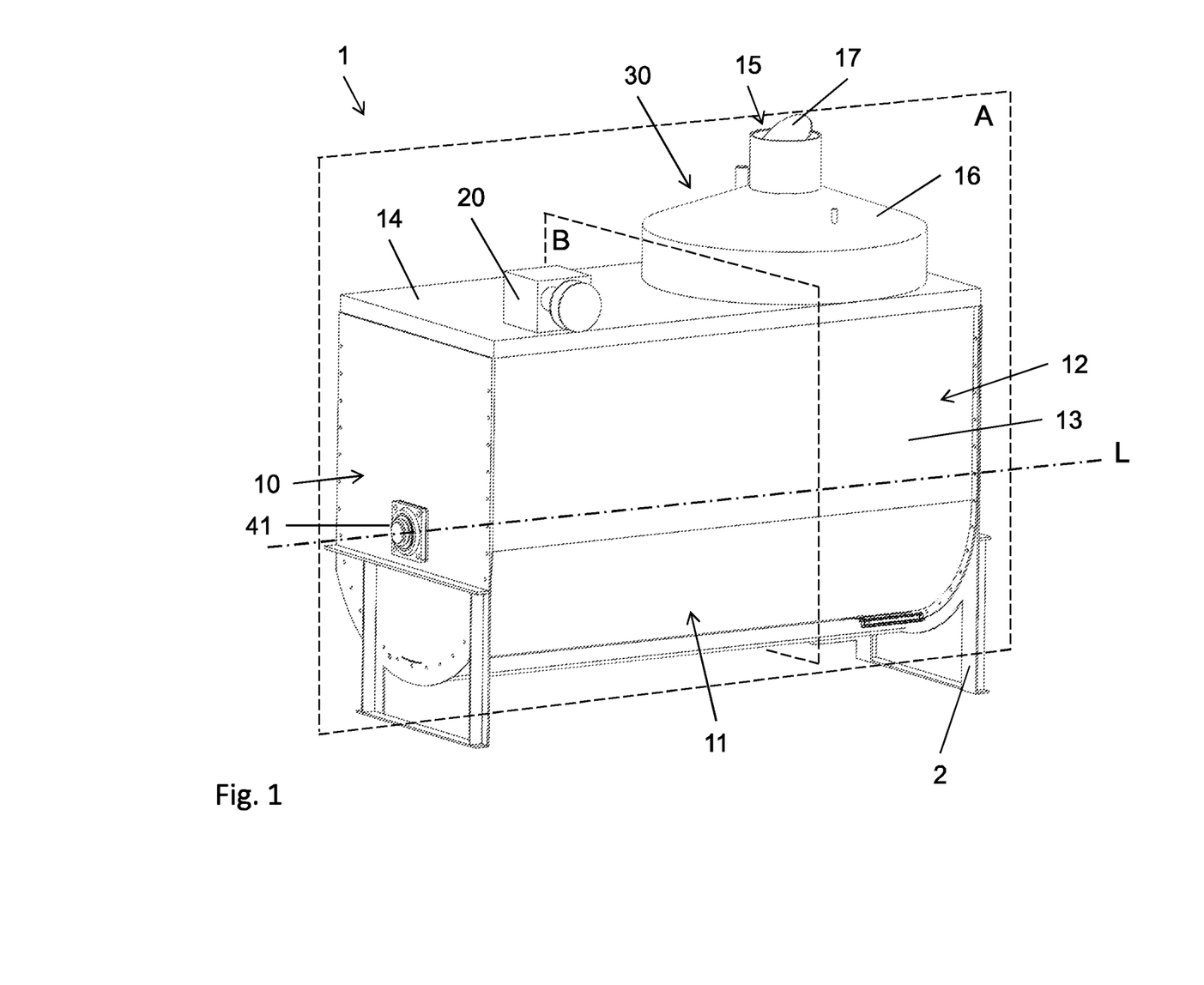
FIG. 1 schematically depicts an embodiment of the breeding system according to the invention, seen in perspective view, FIG. 2 schematically depicts a longitudinal cross section of the breeding system from FIG. 1, along plane A in FIG. 1, FIG. 3 schematically depicts a cross section of the breeding system from FIG. 1, along plane B in FIG. 1, and FIG. 4 schematically depicts, in perspective view, an embodiment of the protein production system according to the invention.

FIG. 1 schematically depicts an embodiment of the breeding system, generally denoted by reference numeral 1. The breeding system 1 is configured to facilitate the growth of crawling insects, in particular insect larvae in an interior thereof.

The breeding system 1 comprises a drum 10, in which the insect larvae are intended to be grown. The drum 10 is, in the present embodiment, an at least partially curved shell, wherein the insects are to be received at the concave side of the shell.

The system 1 comprises a support frame 2, onto which the drum 1 is mounted and which is configured to hold the drum 10 in a stationary position with respect to the surroundings.

The drum 10 has a semi-cylindrical shape. With semi-cylindrical, it is meant that the drum partly has a cylindrical shape and that the rest of the drum 10 has a non-cylindrical shape.

In the present embodiment, a bottom part 11 of the drum 10 is a cylindrical part. An elongate axis of the cylindrical part 11 extends, at least in an operational position of the system 1, in a horizontal direction. The cylindrical part 11 of the drum 10 thereby extends in the horizontal direction and is curved around an axis (L) that is aligned parallel to the horizontal direction.

The cylindrical part 11 of the drum 10 is, in the present embodiment, curved around the axis (L) for 180°. The cylindrical part 11 is aligned such, that a first portion of the cylindrical part, on one side of a vertical plane (A) through the axis (L), is a mirror image of a second portion of the cylindrical part 11, on another side of the vertical plane (A). As such, a concave interior of the cylindrical part 11 is opened-up and accessible from above, in a downwards vertical direction. An upper side of the cylindrical part 11 has, in a horizontal plane, a rectangular cross section.

A top part 12 of the drum 10 has, in the horizontal plane, a rectangular cross section as well, which substantially corresponds to the rectangular cross section of the upper side of the cylindrical bottom part 11.

The top part 12 comprises four wall elements 13, which together form a drum wall. The wall elements 13 extend in the vertical direction and are, in the horizontal plane, arranged such, that they form the rectangular cross section.

In the present embodiment, the height of the wall elements 13, in the vertical direction, is similar, but preferably larger, than the radius of the cylindrical part 11.

In alternative embodiments, the drum may have a fully cylindrical shape. However, the present semi-cylindrical shape of the drum 11 provides the advantage that the interior of the drum 11 becomes better accessible from above.

On top of the top part 12 of the drum 10, a cover part 14 is arranged. With the cover part 14, the interior of the drum 10 is substantially closed-off from the surroundings. In the present embodiment, the cover part 14 is a flat, horizontal plate. It is however understood that in alternative embodiments, the cover part may have a different shape, for example a dome-like shape.

In the cover part 14, an entrance 15 is arranged, through which insects and/or feed may be inserted into the interior of the drum 10. Below the entrance 15, a buffer 16 is arranged, in which the insects and/or feed, to be inserted in the drum 11, may be buffered, before they actually enter the interior of the drum 10. With this buffering, the timing and/or rate of insertion into the drum 10 may be controlled better, as compared to when the insects and/or feed were to be fed in the drum 10 directly.

In an opening of the entrance 15, a valve 17 is provided, with which the opening may be closed-off. As such, access towards the interior of the drum 10 is prevented and the interior of the drum 10 becomes separated from the surroundings. By closing off the interior of the drum 10, the local conditions therein may be maintained better and are less prone to external disturbances.

A control unit 60 is arranged outside the interior of the drum 10. The control unit 60 is configured to measure and, if necessary adapt, climate conditions in the interior of the drum 10 in order to optimize the growing conditions for the insects. Preferably, the control unit 60 may even be configured to adapt the climate conditions onto the needs on a specific type of insects to be grown.

The breeding system 1 comprises a ventilation device 20, which is arranged on the cover part and is configured to exchange air between the interior of the drum 10 and the surroundings. The ventilation device may thereto comprise pumping means, with which ambient air may be pumped in to the interior of the drum 10, thereby forcing air, that was already present in the drum 10 interior, out. As such, any gaseous waste, and possibly liquid waste as well, is removed from the drum 10.

With the ventilation device, it is furthermore achieved that the interior of the drum 10, and in particular the insects that are arranged therein, may be cooled. The ambient air generally has a temperature that is lower than the temperature of the air in the interior of the drum 10. By pumping this colder air into the drum 10, the overall temperature therein is lowered. Additionally, heat may be exchanged form the insects towards the air.

In case, for example, the ambient temperature is higher than the temperature in the interior of the drum 10, the ambient air may be cooled by the ventilation device, before it is pumped into the interior of the drum 10. By doing so, a similar cooling effect as described above may be achieved in the end.

To provide for better control of the temperature in the interior of the drum 10, the present embodiment of the system 1 comprises a temperature sensor 61. The temperature sensor 61 is configured to measure the temperature in the interior of the drum 10, preferably the temperature of the insects therein, on the basis of which the control unit 60 is configured to determine whether additional cooling is required to lower the temperature of the insects.

In the present embodiment, the temperature sensor 61 is arranged in the bulk of the insects, so that the measured temperature is the temperature of the insects in the bulk. These insects, which are surrounded by other insects and are spaced from any of the drum walls, generally have the highest temperatures, so that their temperatures may be considered as a worst case scenario for all the insects in the drum 10.

The system 1 comprises a feeding device 30, which is configured to feed nutrients towards the insects, into the interior of the drum 10. In the present embodiment, the feeding device 30 is integrated with the entrance 15, such that only a single opening needs to be arranged to insert both insects and nutrients into the interior of the drum 10.

In the present embodiment, although not displayed in the figures, the feeding device 30 further comprises a hopper, which is intended to be arranged adjacent the drum 10. In the hopper, a storage for the nutrients may be provided from which, when there is a demand to do so, the nutrients may be transported towards the insects.

For transporting the nutrients from the hopper, a transport screw or auger may be provided, which is configured to forward the nutrient through a tube towards the drum 10. By doing so, the hopper may be set at a distance from the drum 10, so that for example the filling of the hopper, when all of the nutrients therein have been supplied to the insects, becomes easier due to improved accessibility.

It is understood that, in alternative embodiments, the hopper may not necessarily be arranged adjacent the drum, but that it may, for example, be arranged on top of the drum. Additionally, other means for transporting the nutrients from the hopper towards the drum, other than the transport screw or auger, may be provided in an alternative embodiment of the system.

In an embodiment, the system is further configured to supply fluid nutrients to the insects. For supplying fluid nutrients, a fluid feeding device may be provided, which may be arranged adjacent the feeding device for solid nutrients. Such a fluid feeding device may comprise a pump and tubing elements, for pumping the fluid from a storage tank towards the drum.

In a further alternative embodiment, the nutrients may be fed into the interior of the drum through a different opening than the entrance. Additionally, any solid nutrients may, depending on the needs of the insects, be mixed with fluid nutrients in a certain mixing composition.

Besides the temperature sensor 61, the system 1 comprises a humidity sensor 62 and a moisture sensor 63, which are operatively connected to the control unit 60 as well. Based on a measured value of the humidity in the drum 10 or the moisture level of the insects, the control unit 60 is further configured to control a fluid supply towards the insects in order to regulate the humidity and the moisture level.

The system 1 further comprises a ribbon mixer 40 as a shuffling device. The ribbon mixer 40 is arranged in the interior of the drum 10 and is, with respect to the drum 10, rotatable around the axis (L). On one side of the drum 10, the mixer 40 is suspended in a ball bearing 41, to facilitate relative rotation between the mixer 40 and the drum 10. On another, opposite, side of the drum 10, the mixer 40 is driven by a motor 42. On this side, the mixer 40 is suspended in the drum 10 as well.

Figure 2:
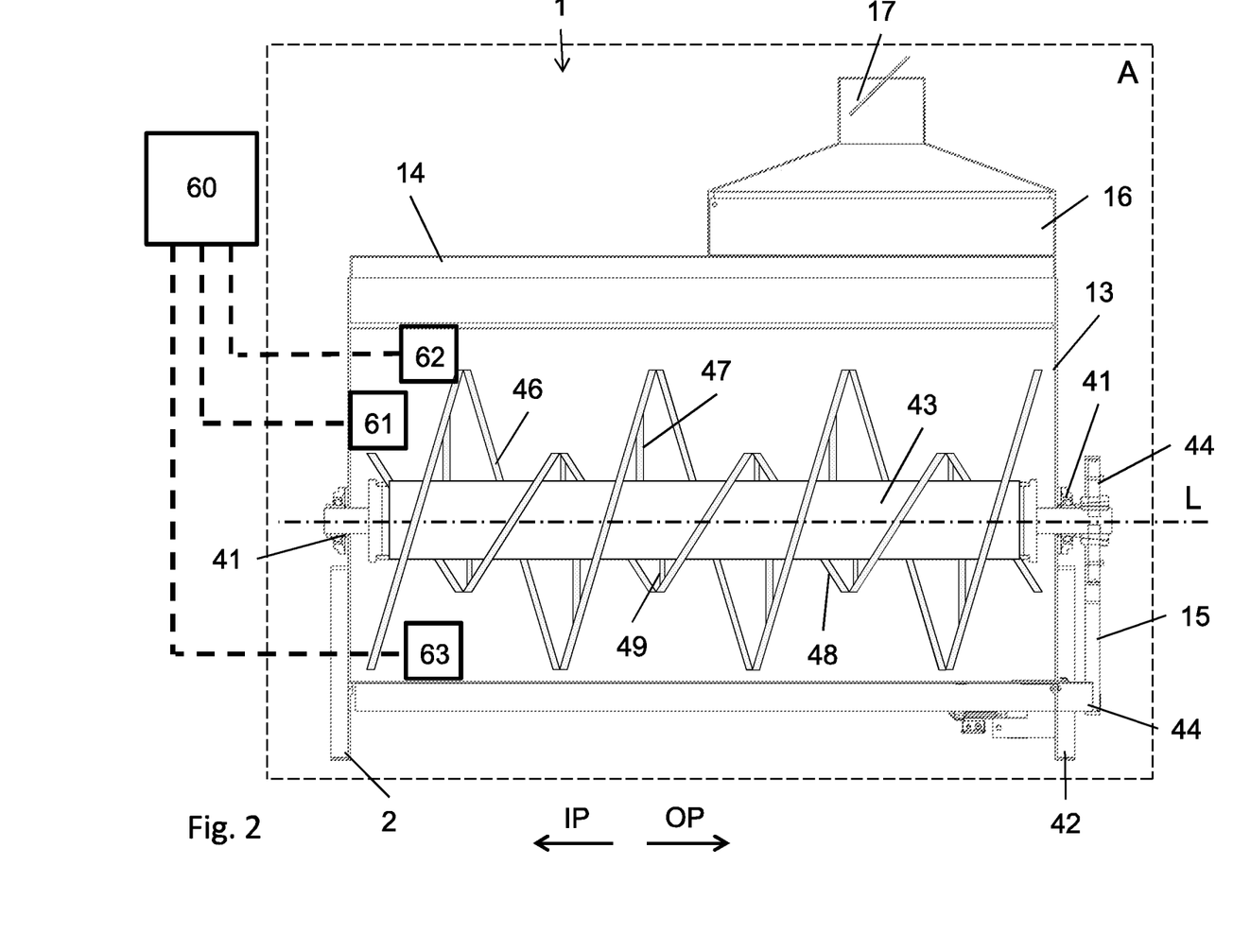
Figure 3:
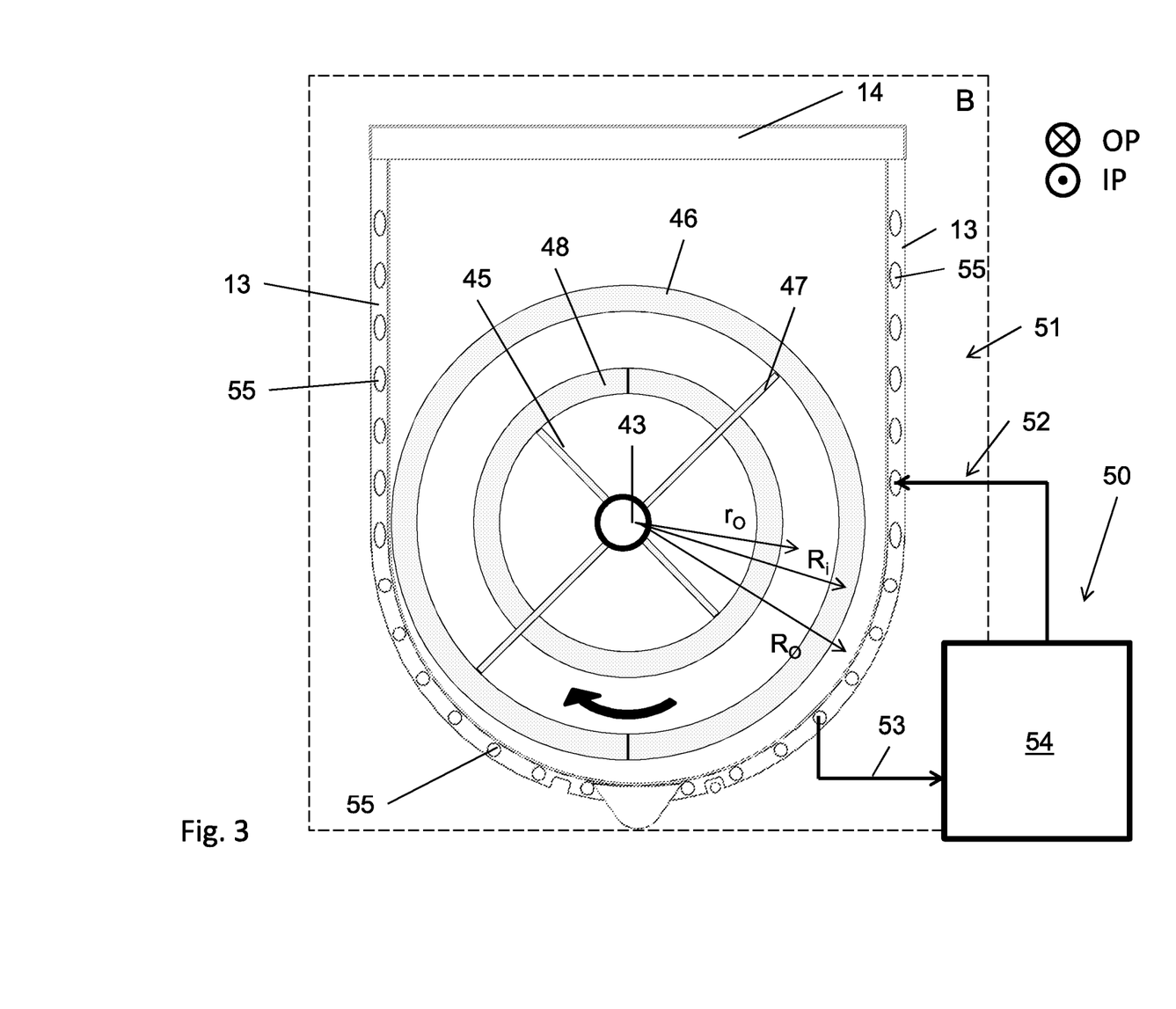

In FIGS. 2 and 3, the mixer 40 is displayed in more detail. In FIG. 2, a longitudinal cross section of the system 1 is displayed the vertical plane (A), parallel to the axis (L). In FIG. 3, a transverse cross section of the system 1, perpendicular to the cross section of FIG. 2, is displayed in a vertical plane (B), perpendicular to the axis (L).

As is best displayed in FIG. 2, the spiral mixer 40 comprises a shaft 43, which extends through the drum 10 along the axis (L). The shaft 43 is rotatably mounted within the drum 10, and is rotatable around the axis (L).

On one side of the shaft 43, displayed left in FIG. 2, it is suspended in the ball bearing 41 in the drum 10 and it slightly extends through the wall element 13 of the drum 10. On the other end of the shaft 43, displayed on the right, the shaft 43 further extends through the wall element 13. On this other end, the shaft 43 is suspended in a ball bearing 41 as well and a sprocket 44 is mounted to the shaft 43.

The motor 42 is an electric motor, which is arranged underneath the drum 10 and comprises a sprocket 44 as well. The motor 42 is connected to the shaft 43 via a chain 45 that runs along toothed outer contours of the sprockets 44. Upon rotation of the motor 42, the rotational movement is transmitted to the shaft 43, through the sprockets 44 and chain 45, which will result in a corresponding rotation of the shaft 43.

In an alternative embodiment, the motor may be directly coupled to the shaft. Furthermore, the motor is not necessarily an electric motor, but may for example be a hydraulic motor.

The ribbon mixer 40 comprises an outer ribbon 46, which is fixedly mounted to the shaft 43 by means of at least one outer spoke 47, extending radially outward from the shaft 43 towards the outer ribbon 46.

The outer ribbon 46 has a thread-like shape, which spirally extends along the axis (L) and the shaft 43. The mixer 40 is, as a result of its spirally-shaped outer ribbon 46, configured to move matter in a direction parallel to the axis (L), upon rotation of the mixer 40 around this axis (L).

In the embodiment, an outmost radius ($R_o$) of the outer ribbon 46 is chosen substantially similar to the radius of the cylindrical part 11 of the drum 10. Since the shaft 43 of the ribbon mixer 40 is aligned concentrically with the axis (L), an outmost radius of the outer ribbon 46 thus travels closely along the concave inner surface of the bottom, cylindrical part 11 of the drum 10 upon rotation of the mixer 40. As such, it is achieved that insects, which are arranged in the interior drum 10, close against the wall, will still be shuffled by the mixer 40.

The ribbon mixer 40 further comprises an inner ribbon 48, which is, just as the outer ribbon 46, fixedly mounted to the shaft 43 of the mixer 40 by means of at least one inner spoke 49.

The inner ribbon 48 extends, just as the outer ribbon 46, spirally along the shaft 43. The inner ribbon 48 is therefore configured to move the insects in a direction parallel to the axis (L) as well, upon rotation of the mixer 40. However, the winding direction of the inner ribbon 48 is in the opposite direction as the winding direction of the outer ribbon 46. Upon rotation of the mixer 40, the outer ribbon 46 is thus configured to move the insects in a first direction, whereas the inner ribbon 48 is configured to move the insects in a second direction, which opposes the first direction.

For example, during clockwise rotation of the shaft 43, as is best seen in FIG. 3, the outer ribbon 46 is configured to move the insects in an outer propulsion direction (OP), whereas the inner ribbon 48 is configured to move the insects in an inner propulsion direction (IP).

In FIG. 3, it is further displayed that, in the present embodiment, an outmost radius ($r_o$) of the inner ribbon 48 is substantially smaller that an inmost radius ($R_i$) of the outer ribbon 46. As such, a projected displacement area of the outer ribbon 46 does not overlap with a projected displacement area of the inner ribbon 48, when seen along the axis (L). During shuffling with the ribbon mixer 40, the insects are thus moved in a first direction with the outer ribbon 46 and are, when they reach a wall element 13 of the drum 10, forced upwards by the outer ribbon 48. Then, they interact with the inner ribbon 48 and they are moved in the opposite direction until they reach an opposite wall element 13 of the drum 10.

For shuffling the insects in the interior of the drum, alternative embodiments may comprise alternative shuffling devices. For example, a transport screw or an auger may be provided in the drum. However, the shuffling with these types of shuffling devices has been found to be less efficient.

The system 1 according to the invention, as is in particular displayed in FIG. 3, comprises a cooling device 50, configured to cool the insects in the interior of the drum 10. This cooling may, in certain phases during the growth of the insects, be required in order to achieve and maintain optimal growing conditions for the insects, since a high amount of heat is produced by the insects during their growth, giving rise to an increase in temperature.

The cooling device 50 comprises a cooling circuit 51, which is at least partially arranged in the wall elements 13 of the drum 10. The cooling device 50 is configured to induce a flow of cooling fluid through the cooling circuit 51, schematically displayed in FIG. 3 by a fluid inlet line 52 and a fluid exit line 53. With a heat exchanger 54, the cooling device 50 is configured to lower the temperature of the cooling fluid and to withdraw heat from the fluid towards the ambient air.

During operational use of the system 1, the heat exchanger 54 is configured to lower the temperature of the cooling fluid below a temperature of the insects in the drum 10. When the temperature of the fluid has reached a sufficiently low level, the fluid is pumped into the fluid circuit 51 through the fluid inlet line 52. With the relatively cold fluid in the cooling circuit 51, within the wall elements 13 of the drum 10, heat is withdrawn, through the wall elements 13, towards the fluid, of which the temperature the increases.

At a certain moment, the fluid has flown through the entire cooling circuit 51 and its temperature has been increased, preferably up to a temperature level that is similar to that of the insects in the interior of the drum 10. The cooling device 50 is then configured to guide the fluid, through the fluid exit line 53, back towards the heat exchanger 54, where the temperature of the fluid is again lowered.

The cooling device 50 thus comprises a closed circuit for the fluid, which is configured to circulate there through and to be heated and cooled. As a result of the active cooling with this cooling device 50, a higher amount of heat may be withdrawn from the insects, when compared to previous cooling processes, which, for example, solely relied on the circulation of air through the drum.

As an alternative to the cooling circuit 51 in the wall elements 13 of the drum 10, a heat exchanger element could as well be placed within the bulk of the insects in the interior of the drum. However, by providing the cooling circuit 51 in the wall elements 13 of the drum 10, a relatively large area, through which heat is transported from the insects, may be provided, since the entire wall, or at least the entire portion of the wall that is in contact with the insects, may function as an area for heat exchange.

In the embodiment that is shown in the figures, the cooling circuit 51 comprises a plurality of fluid channels 55, which are aligned substantially parallel to each other in the drum wall. The channels 55 thereby extend through the drum wall in a direction parallel to axis (L). The cooling fluid is thereby configured to flow through the channels 55 in a direction parallel to the axis (L) as well.

In a further embodiment, the channels of the cooling circuit may be alternatingly arranged in the drum wall. With alternating, it is meant that a direction of flow of the fluid in adjacent channels in the opposite direction.

In the present embodiment, the cooling device 50 is configured to be controlled by the control unit 60, on the basis of the measured temperature of the insects. In particular, the control unit 60 comprises a feedforward device is provided. The feedforward device is configured to control the cooling device 50, to adjust the temperature in the interior of the drum 10, on the basis of a predicted growth profile of the insects. With the growth profile, the required amount of cooling and nutrients can be determined, such that the control unit 60 can act thereon in a feedforward manner.

The combination of cooling the insects in the interior of the drum 10, by means of a cooling circuit 51 in the drum wall, and the shuffling of the insects through the interior of the drum 10, provides for a homogenised temperature profile of the insects in the drum 10. In case the system would lack a shuffling device, only the temperature of insects in the vicinity of the drum wall is lowered, since the cooling circuit 51 is arranged therein, is lowered, whereas virtually no heat is withdrawn from the insects in the bulk.

Figure 4:
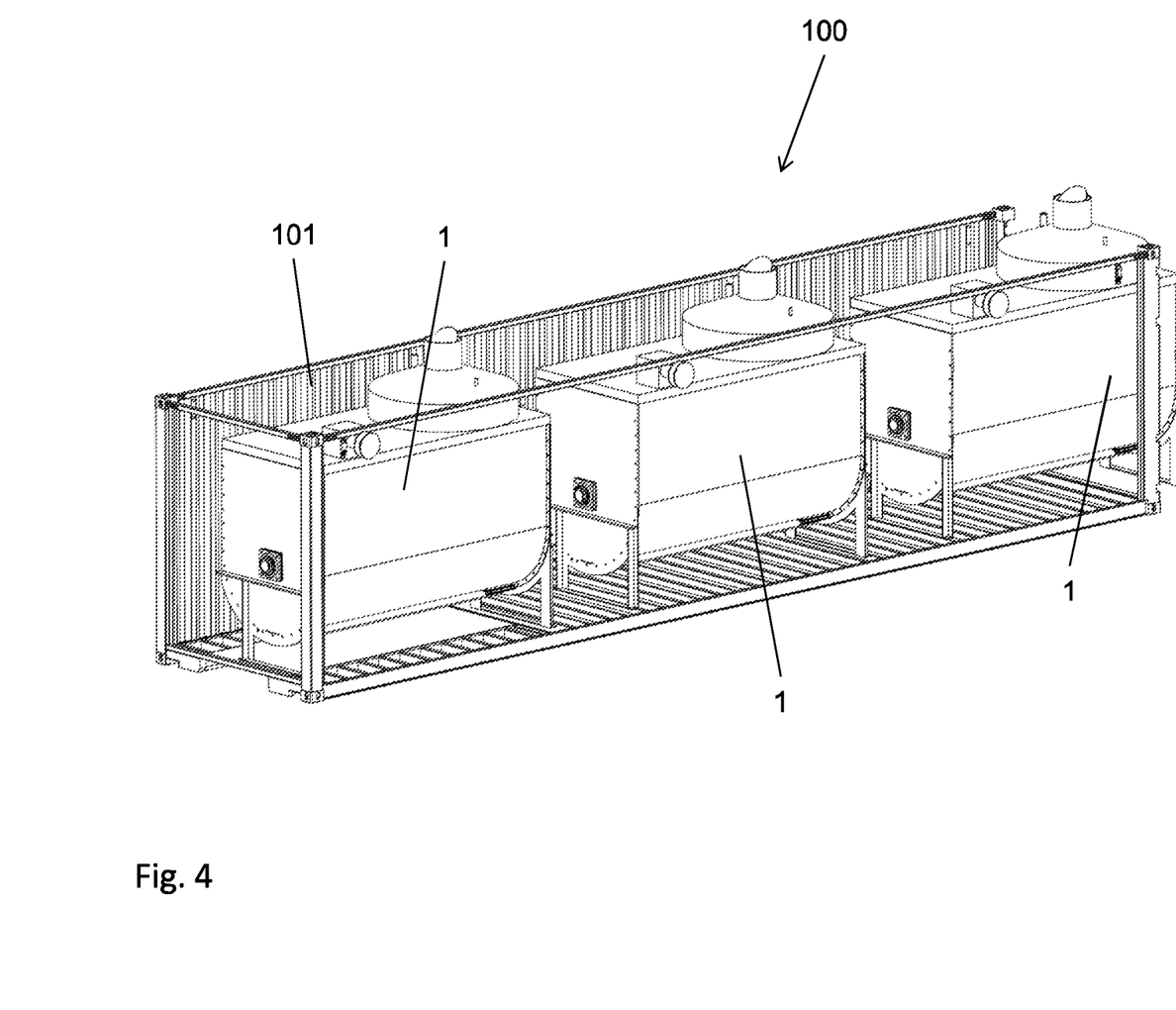

In FIG. 4, a partially opened-up view on an embodiment of the protein production system according to the invention is displayed, denoted by reference numeral 100.

The embodiment of the protein production system 100 comprises three breeding systems 1. The breeding systems 1 are arranged adjacent each other within a shipping container 101.

The combining of three breeding systems 1 is a single protein production system 100 provides the advantage that, although the individual breeding systems 1 are configured to discharge insects in a batch-wise manner, the protein production system 100 is configured to provide insects, to be for example used as animal feed, in a continuous manner.

By integrating the breeding systems 1 in a shipping container 101, the protein production system 100 becomes more compact, and better to transport, as compared to when the breeding systems had to be transported and installed separately.

The protein production system 100 may additionally comprise a second shipping container in which a fly cage and an egg-laying device are provided for each of the breeding systems. The second shipping may be arranged on top of the first shipping container, so that ungrown insects may be easily transferred from the egg-laying device towards the breeding systems.

The invention claimed is:

1. Breeding system for the breeding of crawling insects, optionally insect larvae, comprising:
   a drum, comprising at least one wall, defining a drum interior, to house the insects,
   a shuffling device, arranged at least partially in the drum interior, to shuffle insects in the drum interior,
   a feeding device, to feed nutrients into the drum interior,
   wherein the system comprises a cooling device having a cooling fluid circuit that is, by means of a flow of coolant in the circuit, configured to withdraw heat from the drum interior,
      wherein the drum is non-rotatably fixed with respect to the surroundings of the drum, and
      wherein the shuffling device is movable with respect to the drum making shuffling insects in the drum interior possible without movement of the drum.

2. Breeding system according to claim 1, comprising a control unit having a feedforward device that is adapted to control the cooling device and the feeding device on the basis of a predicted growth profile of the insects, in order to control the temperature in the drum interior.

3. Breeding system according to claim 2, wherein the control unit is configured to control the temperature in the drum interior.

4. Breeding system according to claim 2, wherein the control unit is configured to control the feeding device in order to feed a desired mass of nutrients to the insects in the interior of the drum, on the basis of the amount of the insects in the interior of the drum.

5. Breeding system according to claim 1, comprising at least one temperature sensor, to measure a temperature in the drum interior and to transmit a signal based on this temperature, and a control unit, wherein the control unit is configured to control the temperature in the drum interior and to control the cooling device, based on the measured temperature.

6. Breeding system according to claim 1, wherein the cooling fluid circuit is arranged at least partially in the at least one wall of the drum.

7. Breeding system according to claim 1, wherein the shuffling device is configured to shuffle insects in the drum interior, in order to homogenize the withdrawal of heat from the drum interior.

8. Breeding system according to claim 1, comprising a humidity sensor to measure the humidity in the drum interior.

9. Breeding system according to claim 1, comprising a moisture sensor to measure the moisture level in the drum interior.

10. Breeding system according to claim 1, wherein the drum comprises a discharge opening in the at least one wall, through which the shuffling device is configured to discharge insects from the drum interior.

11. Breeding system according to claim 10, wherein the shuffling device is configured to discharge substantially all insects from the drum interior, in a batch wise manner, when the insects have grown up to a certain size.

12. Breeding system according to claim 1, comprising a fly cage and an egg-laying device, which are both arranged on top of the drum and wherein flies from the fly cage are allowed to lay eggs in the egg-laying device.

13. Breeding system according to claim 12, wherein the egg-laying device is configured to deposit eggs into the drum interior.

14. Protein production system, for the on-site production of protein-rich insect larvae as animal feed, comprising two or more breeding systems according to claim 1, which are arranged in a predefined space, configured to discharge living larvae.

15. Protein production system according to claim 14, comprising three or more breeding systems in the predefined space, wherein the predefined space has the dimensions of a standard-sized forty-feet shipping container.

16. Method for the breeding of crawling insects, comprising the steps of:
arranging insects eggs and/or insects that have been hatched from the eggs in an interior of a non-rotatable drum,
shuffling insects that were hatched from the eggs to homogenise a temperature of the insects without movement of the drum, and
feeding the insects,
wherein the method comprises the step of cooling the insects in the interior of the drum with a flow of coolant in a cooling circuit of a cooling device.

17. Method according to claim 16, comprising the step of measuring the temperature of the insects and of controlling the amount of cooling with the cooling device, based on the measured temperature.

18. Method according to claim 17, comprising the step of controlling of the cooling device and of the feeding on the basis of a predicted growth profile of the insects, thereby controlling the temperature in the drum interior.

19. Method according to claim 16, comprising the step of loading the eggs in the interior of the drum from an egg-laying device.

20. Method according to claim 16, comprising the step of discharging the insects from the interior of the drum when the insects have grown up to the predetermined size.

21. Method according to claim 16, comprising the step of measuring temperature, humidity and/or moisture level in the interior of the drum.

22. Method according to claim 21, comprising the step of controlling the amount of cooling of the interior and the amount of feeding to the insects, based on the measured temperature, humidity and/or moisture level.

* * * * *